(12) United States Patent
Comerota et al.

(10) Patent No.: US 8,702,678 B2
(45) Date of Patent: Apr. 22, 2014

(54) ASSEMBLIES, SYSTEMS, AND METHODS FOR INFUSING THERAPEUTIC AGENTS INTO THE BODY

(75) Inventors: Anthony J. Comerota, Perrysburg, OH (US); Thomas J. Fogarty, Portola Valley, CA (US); Jonathan M. Olson, San Jose, CA (US); Richard A. Lotti, Santa Cruz, CA (US)

(73) Assignee: Venous Therapy, Inc., Mountain View, CA (US)

( * ) Notice: Subject to any disclaimer, the term of this patent is extended or adjusted under 35 U.S.C. 154(b) by 25 days.

(21) Appl. No.: 13/564,608

(22) Filed: Aug. 1, 2012

(65) Prior Publication Data
US 2013/0085381 A1    Apr. 4, 2013

Related U.S. Application Data

(60) Provisional application No. 61/514,728, filed on Aug. 3, 2011.

(51) Int. Cl.
| | | |
|---|---|---|
| A61M 25/09 | (2006.01) | |
| A61M 25/10 | (2013.01) | |
| A61M 5/14 | (2006.01) | |

(52) U.S. Cl.
USPC ............... 604/507; 604/96.01; 604/103.05

(58) Field of Classification Search
CPC .............. A61M 25/10; A61M 2025/0024; A61M 2025/0025; A61M 2025/1052; A61M 2025/1081
USPC .......... 604/96.01, 103.05, 907, 915; 606/194
See application file for complete search history.

(56) References Cited

U.S. PATENT DOCUMENTS

| | | | | |
|---|---|---|---|---|
| 4,968,306 | A | * | 11/1990 | Huss et al. ............... 604/264 |
| 5,702,372 | A | * | 12/1997 | Nelson ................ 604/264 |
| 6,350,253 | B1 | * | 2/2002 | Deniega et al. ......... 604/164.02 |
| 6,575,932 | B1 | | 6/2003 | Obrien et al. |
| 6,695,811 | B2 | | 2/2004 | Samson et al. |
| 7,537,580 | B2 | | 5/2009 | Willard |
| 2003/0032942 | A1 | * | 2/2003 | Theeuwes et al. ........... 604/537 |
| 2004/0073159 | A1 | | 4/2004 | Nelson |
| 2009/0254064 | A1 | | 10/2009 | Boatman |
| 2010/0228333 | A1 | * | 9/2010 | Drasler et al. ............... 623/1.11 |

OTHER PUBLICATIONS

International search report and written opinion dated Oct. 16, 2012 for PCT/US2012/049322.

* cited by examiner

*Primary Examiner* — Quynh-Nhu H Vu
(74) *Attorney, Agent, or Firm* — Wilson Sonsini Goodrich & Rosati

(57) ABSTRACT

An infusion catheter assembly has the ability to infinitely titrate the length of a porous fluid distribution section in situ. The infusion catheter assembly thereby provides a length of infusion that can be infinitely varied over a prescribed range, to control the effective infusion length and the rate of infusion. Using the infusion catheter assembly, a physician has the capability to treat only the length of the vessel desired, thereby preventing excessive drug/patient exposures. The porous fluid distribution section can include an array of spaced apart apertures that vary in size and/or density along the length of the porous fluid distribution section, such that the flow rate remains essentially constant for a given inlet pressure independent of the effective infusion length.

29 Claims, 9 Drawing Sheets

$$F = \sum_{1-n} A_n / t$$

ASSEMBLIES, SYSTEMS, AND METHODS FOR INFUSING THERAPEUTIC AGENTS INTO THE BODY

CROSS-REFERENCE

The present application is a non-provisional of and claims the benefit of U.S. Provisional Patent Application No. 61/514,728 filed Aug. 3, 2011; the entire contents of which is incorporated herein by reference.

BACKGROUND OF THE INVENTION

1. Field of the Invention

The present invention generally relates to medical devices and methods. More particularly, the present invention is related to the delivery of therapeutic agents into the body.

2. Background

Infusion catheters are known, which provide the administration of various therapeutic agents in solutions into the peripheral vasculature. Conventional designs usually contain inner and outer catheter shafts. The outer catheter shaft provides a series of holes over a prescribed length through which the agent(s) can be administered to the vessel and surrounding tissue or disease. Conventional technology is focused on the shape and/or density of the holes for infusion, and/or providing a zone of infusion by blocking a segment of the vessel, and/or providing a guide wire lumen. While this technology is promising, improved devices and method are still needed to provide catheters or other therapeutic agent delivery systems that deliver the therapeutic agent to a specific target site and with better control of infusion rates. At least some of these objective will be met by the embodiments disclosed herein.

SUMMARY OF THE INVENTION

One aspect of the invention provides an infusion catheter assembly having the ability to infinitely titrate the length of the infusion section in situ. The infusion catheter assembly provides a length of infusion that can be infinitely varied over a prescribed range, to control the effective infusion length and the rate of infusion. Using the infusion catheter assembly, a physician has the capability to treat only the length of the vessel desired, thereby preventing excessive drug/patient exposures.

Another aspect of the invention provides an infusion catheter assembly having a porous fluid distribution section that includes an array of spaced apart apertures that vary in size and/or density along the length of the porous fluid distribution section. A barrier mechanism can be provided that is movable along the porous distribution section to establish for the infusion catheter assembly an infinitely variable range of effective infusion lengths between a maximum length and any smaller length along the porous fluid distribution section. The spaced apart apertures vary in size and/or density in a predetermined fashion along the maximum length such that the flow rate remains essentially constant for a given inlet pressure independent of the effective infusion length.

In another aspect of the present invention an infusion catheter assembly comprises a catheter body having an interior lumen and including a porous fluid distribution section having a predefined maximum length communicating with the interior lumen. The catheter assembly also includes at least one fluid delivery port for dispensing a fluid from an external source into communication with the porous fluid distribution section for infusion through the porous fluid distribution section at a flow rate, and also a barrier mechanism movable within the catheter body to establish for the infusion catheter assembly an infinitely variable range of effective infusion lengths between the maximum length and any smaller length along the porous fluid distribution section.

In another aspect of the present invention, an infusion catheter assembly may comprise a catheter body having an interior lumen and including a porous fluid distribution section having a predefined maximum length communicating with the interior lumen. The porous discharge section may comprise an array of spaced apart apertures that vary in size and/or density along the length of the porous fluid distribution section. The catheter assembly may also have at least one fluid delivery port for dispensing a fluid from an external source into communication with the porous fluid distribution section for infusion through the porous fluid distribution section at a flow rate.

The barrier mechanism may comprise an expandable structure which may expand in response to introduction of a fluid. The barrier mechanism may also be movable within the catheter body to establish for the infusion catheter assembly an infinitely variable range of effective infusion lengths between the maximum length and any smaller length along the porous fluid distribution section. The spaced apart apertures may vary in size and/or density in a predetermined fashion along the maximum length such that the flow rate remains essentially constant for a given inlet pressure independent of the effective infusion length. The assembly may further include a lumen in the catheter body to accommodate passage of a guide wire, and the barrier mechanism may also include a lumen to accommodate passage of the guide wire. A first radiopaque marker may be disposed on the barrier mechanism and a second radiopaque marker may be disposed on the catheter body to visualize the effective infusion length by radiographic imaging.

The porous fluid distribution section may be sized and configured for weep or pulse-spray infusion of the fluid. The catheter body may be sized and configured for intravascular introduction, intramuscular introduction, or introduction into a tissue mass or organ. The fluid dispensed by the fluid delivery port may include a therapeutic agent such as a thrombolytic agent.

The barrier mechanism may include an inner catheter body sized and configured to be manipulated by sliding within the catheter body along the maximum length of the porous fluid distribution section. The inner catheter body may include the at least one fluid delivery port. A barrier structure may be carried by the inner catheter body proximal of the fluid delivery port. The barrier structure may have a reduced dimension condition, which accommodates the sliding manipulation of the inner catheter body along the maximum length of porous fluid distribution section. The barrier structure may have an increased dimension condition, which presses against the interior lumen and forms a barrier wall that blocks flow of the dispensed fluid into communication with the porous fluid distribution section proximal of the barrier wall. The assembly may also have a mechanism to selectively reduce and increase the barrier structure within the outer catheter body anywhere along the maximum length of the porous fluid distribution section to establish for the infusion catheter assembly an infinitely variable range of effective infusion lengths between the maximum length and any smaller length along the porous fluid distribution section.

In yet another aspect of the present invention, an infusion method comprises (i) providing an infusion catheter assembly comprising a catheter body having an interior lumen and including a porous fluid distribution section having a predefined maximum length communicating with the interior lumen. The porous discharge section comprises an array of spaced apart apertures that vary in size and/or density along the length of the porous fluid distribution section. The infusion catheter assembly further comprising at least one fluid delivery port for dispensing a fluid from an external source at an inlet pressure into communication with the porous fluid distribution section for infusion through the porous fluid distribution section at an infusion flow rate, and a barrier mechanism movable within the catheter body to establish for the infusion catheter assembly an infinitely variable range of effective infusion lengths between the maximum length and any smaller length along the porous fluid distribution section. The spaced apart apertures vary in size and/or density in a predetermined fashion along the maximum length such that the flow rate remains essentially constant for a given inlet pressure independent of the effective infusion length. The method also comprises (ii) moving the barrier mechanism within the catheter body to establish a desired effective infusion length, and (iii) infusing a fluid through the desired effective infusion length of the porous fluid distribution section.

The infusing step may include visualizing the effective infusion length by radiographic imaging of a first radiopaque marker on the catheter body and a second radiopaque marker on the barrier mechanism. Infusing may be performed in a blood vessel, a tissue mass or organ, and may include delivery of a therapeutic agent, anesthesia or treatment of an occlusion of thrombus in the vasculature, or treatment of a tumor.

In still another aspect of the present invention, an infusion method comprises (i) providing an infusion catheter assembly comprising a catheter body having an interior lumen and including a porous fluid distribution section having a predefined maximum length communicating with the interior lumen. The infusion catheter assembly further comprises at least one fluid delivery port for dispensing a fluid from an external source into communication with the porous fluid distribution section for infusion through the porous fluid distribution section, and a barrier mechanism movable within the catheter body to establish for the infusion catheter assembly an infinitely variable range of effective infusion lengths between the maximum length and any smaller length along the porous fluid distribution section. The method also comprises (ii) moving the barrier mechanism within the catheter body to establish a desired effective infusion length, and (iii) infusing a fluid through the desired effective infusion length of the porous fluid distribution section.

In still another aspect of the present invention, an infusion catheter assembly comprises an outer catheter body having an interior lumen and including a porous fluid distribution section having a predefined maximum length communicating with the interior lumen. The assembly also comprises an inner catheter body sized and configured, when in use, to be inserted into the outer catheter body and manipulated by sliding within the outer catheter body along the maximum length of the porous fluid distribution section. The inner catheter body includes at least one fluid delivery port for dispensing a fluid from an external source into communication with the porous fluid distribution section for infusion through the porous fluid distribution section. The assembly includes a barrier structure carried by the inner catheter body proximal of the fluid delivery port. The barrier structure has a reduced dimension condition, which accommodates the sliding manipulation of the inner catheter body along the maximum length of porous fluid distribution section, and an increased dimension condition, which presses against the interior lumen and forms a barrier wall that blocks flow of the dispensed fluid into communication with the porous fluid distribution section proximal of the barrier wall. The assembly also includes a mechanism to selectively reduce and increase the dimension of the barrier structure within the outer catheter body anywhere along the maximum length of the porous fluid distribution section to establish for the infusion catheter assembly an infinitely variable range of effective infusion lengths between the maximum length and any smaller length along the porous fluid distribution section.

The infusion catheter assembly may further include an outer radiopaque marker on the outer catheter body and an inner radiopaque marker on the inner catheter body to visualize the effective infusion length by radiographic imagining. The assembly may have a lumen in the inner catheter body to accommodate passage of a guide wire, and the outer catheter body may also include a lumen to accommodate passage of the guide wire. The porous fluid distribution section may comprise an array of axially spaced-apart apertures or pores that communicate with the interior lumen along the maximum length of the porous fluid discharge section. The porous fluid discharge section may be sized and configured for weep or pulse-spray infusion of the fluid.

In another aspect of the present invention, an infusion method comprises (i) providing an outer catheter body having an interior lumen and including a porous fluid distribution section having a predefined maximum length communicating with the interior lumen. The method also includes (ii) inserting into the outer catheter body an inner catheter body having at least one fluid delivery port for dispensing a fluid from an external source into communication with the porous fluid distribution section for infusion through the porous fluid distribution section. The inner catheter body includes a barrier structure proximal of the fluid delivery port, the barrier structure having a reduced dimension condition and an increased dimension condition. The method also includes (iii) manipulating the inner catheter body by sliding the inner catheter body within the outer catheter body when the barrier structure is in a reduced dimension condition along the maximum length of the porous fluid distribution section; (iv) manipulating the inner catheter body by placing the barrier structure in an increased dimension condition to press the barrier structure against the interior lumen and form a barrier wall that blocks flow of the dispensed fluid into communication with the porous fluid distribution section proximal of the barrier wall; (v) performing (iii) and (iv) to selectively reduce and increase the dimension of the barrier structure within the outer catheter body along the maximum length of the porous fluid distribution section to establish for the infusion catheter assembly a desired effective infusion length, wherein the desired effective infusion length is infinitely variable between the maximum length and any smaller length along the porous fluid distribution section; and (vi) infusing a fluid through the desired effective infusion length of the porous fluid distribution section. Step (v) may be performed using a guide wire.

These and other aspects and advantages of the invention are evident in the description which follows and in the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The physical embodiments disclosed merely exemplify the technical features of the invention, which may be embodied in other specific structure. While a preferred embodiment has been described, the details may be changed without departing from the technical features of the invention.

I. The Assembly

Figure 1A:
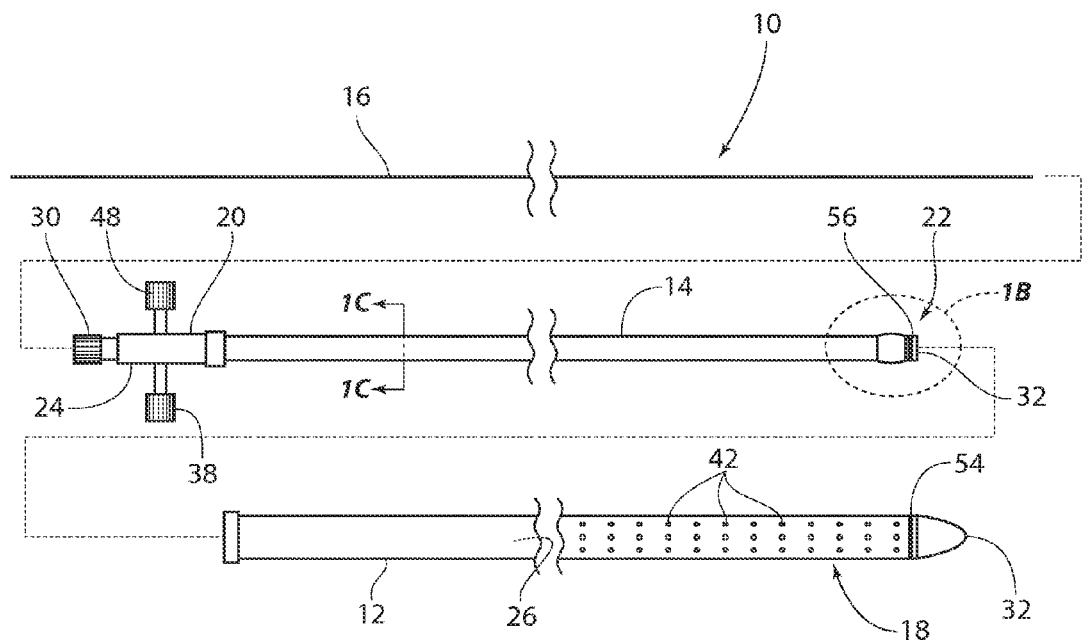
FIG. 1A is an exploded view of an infusion catheter assembly comprising an inner catheter body and an outer catheter body that embodies the technical features of the invention.
Figure 1B:
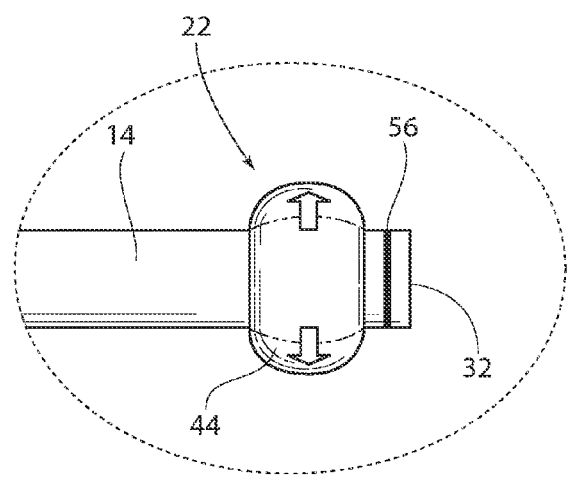
FIG. 1B is an enlarged view of the distal end of the inner catheter body shown in FIG. 1A, showing the presence of a barrier structure.

FIG. 1A shows, in an exploded view, an infusion catheter assembly 10. In FIG. 1A, the infusion catheter assembly 10 is sized and configured for delivering one or more therapeutic agents in solution into the peripheral vasculature. However, the technical features that will be described are not limited to intravascular infusion. Intravascular infusion is but one of many exemplary embodiments illustrating the technical features of the assembly. It should be appreciated that the technical features of the infusion catheter assembly 10 that will be described are applicable for use to achieve diverse infusion therapy or treatment objectives by delivering therapeutic agents to targeted tissue or organ regions by any non-oral route throughout the body, e.g., during surgery, and/or for oncological purposes in the treatment of tumors, and/or whenever subcutaneous, intramuscular, or epidural infusions are desired.

Figure 2A:
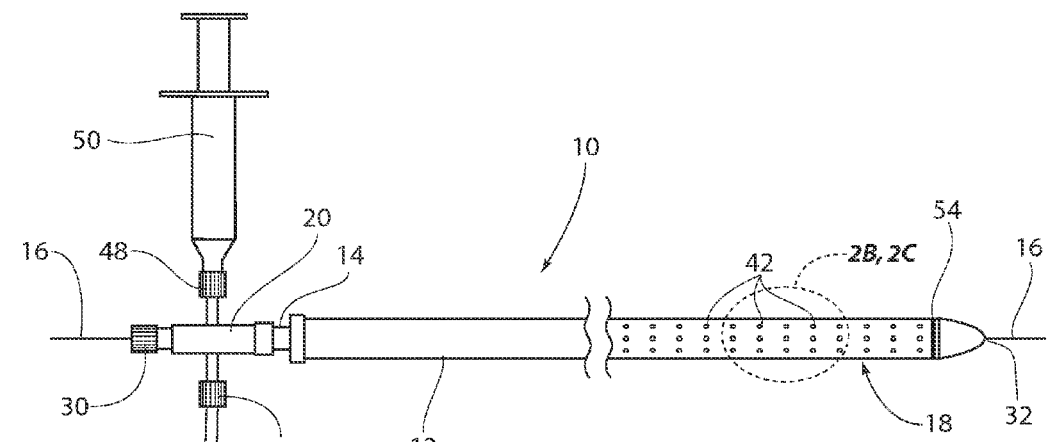
FIG. 2A is an assembled view of the infusion catheter assembly shown in FIG. 1A.

As FIG. 1A shows for exemplary purposes, the assembly 10 includes a first catheter body 12 and a second catheter body 14. As FIG. 2A shows in an assembled view, the second catheter body 14 is sized and configured, when in use, to be inserted into the first catheter body 12. For this reason, the first and second catheter bodies 12 and 14 will also be called, respectively, an outer catheter body 12 and an inner catheter body 14.

Figure 3A:
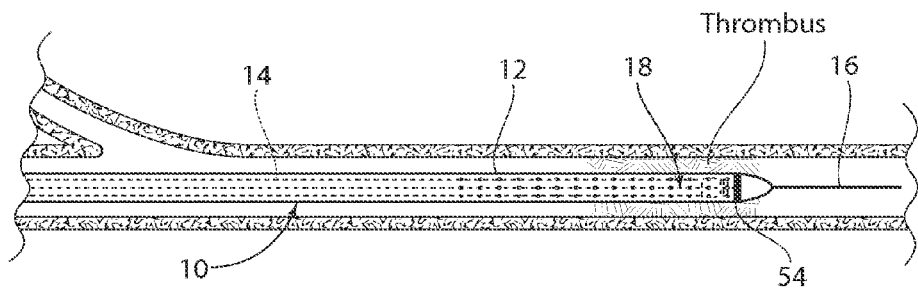
FIGS. 3A to 3E illustrate the use of the infusion catheter assembly shown in FIGS. 1A and 2A to treat an occlusion having a length significantly less than the maximum infusion length of the assembly.

In the exemplary embodiment, as FIG. 2A also shows, the assembly of the inner catheter body 14 and the outer catheter body 12 is sized and configured to be introduced over a conventional guide wire 16 (e.g., 0.035 inch diameter), for delivery into a targeted treatment region in the peripheral vasculature (see FIG. 3A). The targeted treatment region can be within a vein or an artery of the peripheral vasculature, depending upon therapeutic objective desired. The outside diameter of the outer catheter body 12 can be sized, depending upon anatomy of the targeted treatment region e.g., from 4 Fr to 10 Fr. As FIG. 1A shows, the distal end of the outer catheter body 12 is desirably tapered to provide atraumatic access to the targeted tissue region.

The catheter bodies 12 and 14 can comprise, e.g., high or low density polyethylene which has a low friction surface, easing passage over the guide wire 16. Other candidate materials include fluorinated ethylene propylene (FEP), polyether block amide, nylon 12, polyamide, polyamide copolymer, polypropylene, polyester copolymer, polyvinyl difluoride or silicon rubber. The length of the assembly can range, depending upon anatomy of the target treatment region, e.g., from 45 cm or less to 135 cm or more.

In the exemplary embodiment, upon introduction to the targeted treatment region in the peripheral vasculature (see, e.g., FIG. 3E), the assembly 10 is sized and configured to deliver one or more therapeutic agents in solution into the targeted region. In the illustrated embodiment, the therapeutic agent(s) can comprise, e.g., a drug for systemic circulation to treat the individual, or an anesthetic agent, or a lytic agent to dissolve thrombus residing in the targeted treatment region.

For this purpose, the distal region of the outer catheter body 12 includes a porous fluid distribution section 18. The length or area of the section 18 can vary, e.g., between 1 to 3 cm. Residing within the outer catheter body 12, the inner catheter body 14 delivers the therapeutic agent in solution from an external source into communication with the porous fluid distribution section 18 see FIG. 2A). The porous fluid distribution section 18 can be sized and configured, e.g., for weep infusion (regional, continuous, lower pressure delivery) or pulse-spray infusion (directly injected, higher pressure, burst or pulsed delivery) of the therapeutic agent at the targeted treatment site. The source can comprise, e.g., a conventional infusion pump for slow, continuous infusion of the therapeutic agent, or a traditional syringe system for manual and/or burst delivery.

As will be described in greater detail later, the inner catheter body 14 can be manipulated by sliding within the outer catheter body 12 along the length of the porous fluid distribution section 18. By fixing a desired relative position of the inner catheter body 14 along the porous fluid distribution section 18, the effective infusion length or area of the porous fluid distribution section 18 can be titrated in situ (see FIGS. 2E and 2F) anywhere within a range between the maximum length of the porous fluid distribution section 18 and any smaller length of the porous fluid distribution section 18 down to its minimum length.

Figure 2B:
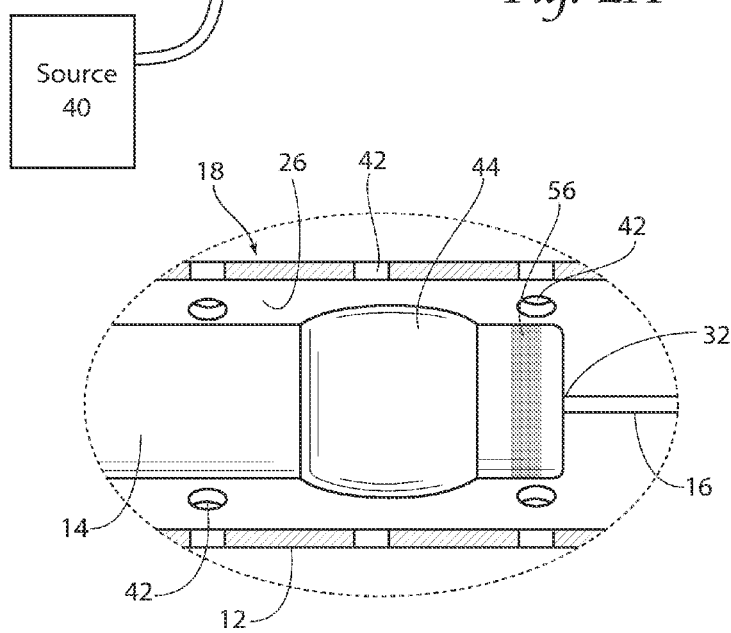
FIGS. 2B and 2C are enlarged views of the distal end of the inner catheter body residing within the outer catheter body, with the barrier structure shown, respectively, in a reduced dimension condition (FIG. 2B) and an increased dimension condition (FIG. 2C), to form a fluid tight seal and define a fluid distribution chamber within the outer catheter body.
Figure 2C:
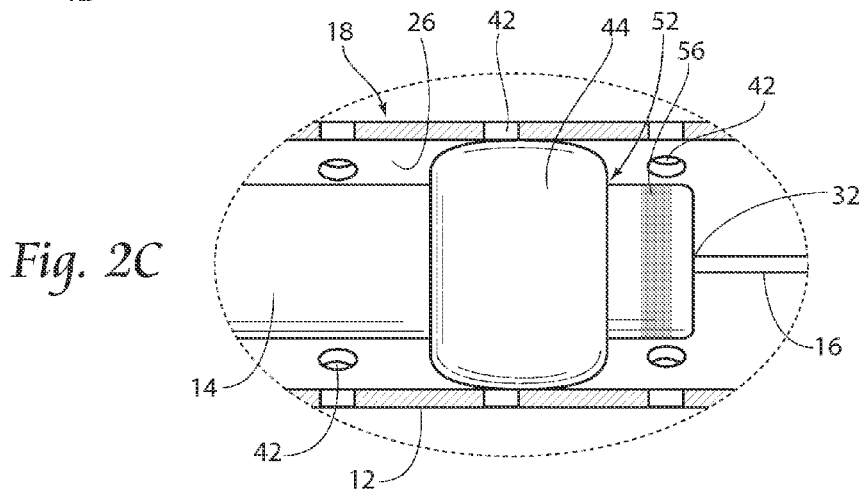
Figure 2D:
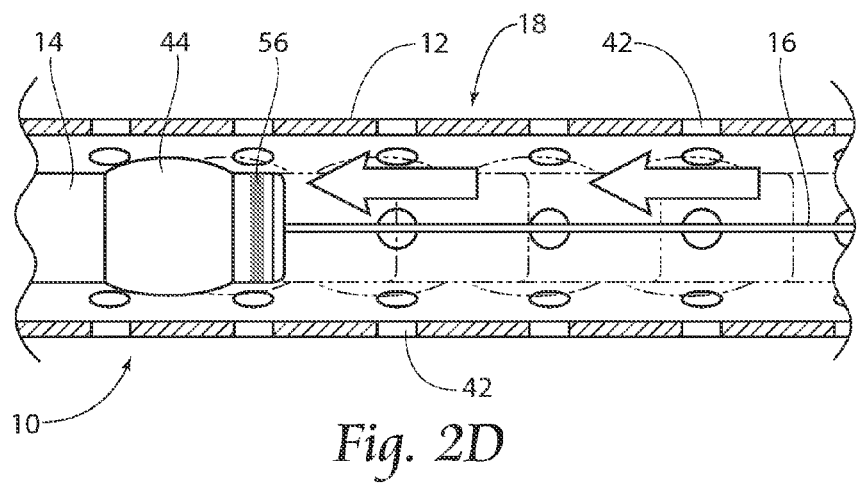
FIG. 2D is enlarged view showing the capability of infinitely moving the distal end of the inner catheter body in situ within the outer catheter body.
Figure 2E:
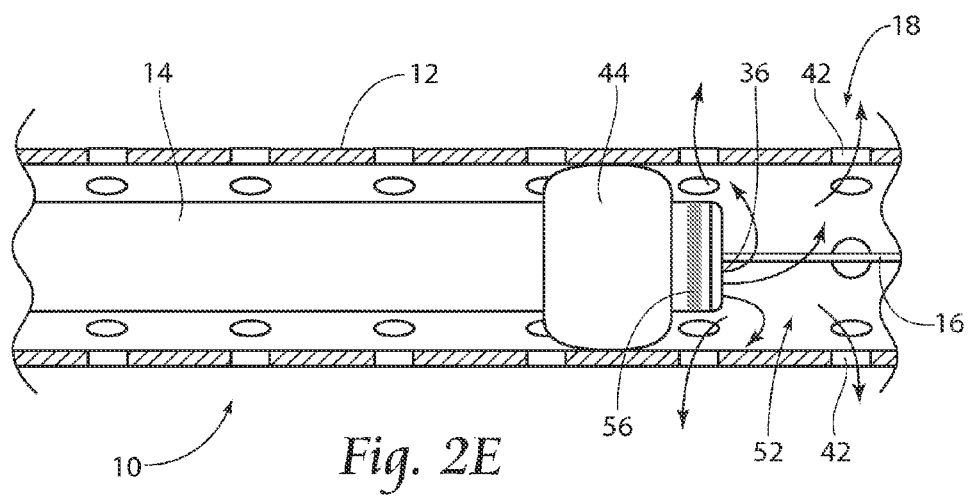
FIG. 2E is an enlarged view of the distal end of the inner catheter body residing at a first position within the outer catheter body, with the barrier structure in its increased dimension condition to form a chamber which distributes therapeutic agent(s) for discharge only by the fluid discharge apertures in the outer catheter body that are distal to (and not proximal of) the location of the fluid tight seal.
Figure 2F:
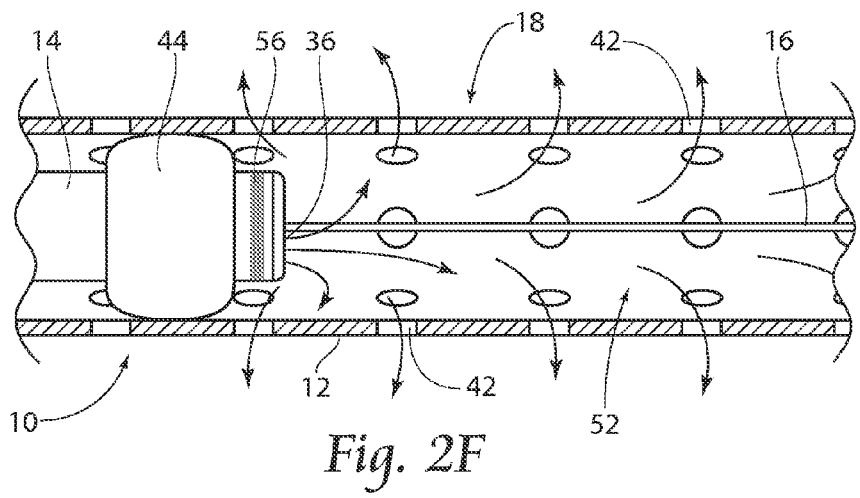
FIG. 2F is an enlarged view of the distal end of the inner catheter body residing at a second position within the outer catheter body, with the barrier structure shown in its increased dimension condition to form a chamber that is larger than the chamber shown in FIG. 2E, which likewise distributes therapeutic agent(s) for discharge only by the fluid discharge apertures in the outer catheter body that are distal to (and not proximal of) the location of the fluid tight seal, the infusion length shown in FIG. 2F being longer than the infusion length shown in FIG. 2E.

According to this aspect of the invention, as exemplified in FIGS. 2E and 2F, manipulating the inner catheter body 14 relative to the outer catheter body 12 makes it possible to infinitely vary in situ the effective infusion length or area of the porous fluid distribution section 18 between zero up to the maximum length provided by the outer catheter body 12. In this way, the distribution of the therapeutic agent(s) can be precisely titrated in situ according to the morphology and delivery demands of targeted treatment region.

The assembly 10 may be variously constructed to include these technical features.

In the embodiment illustrated in FIG. 1A, the inner catheter body 14 includes a proximal end 20 and a distal end 22. A handle 24, sized and configured for manipulation by a caregiver, is attached to the proximal end 20.

The outer catheter body 12 includes an interior lumen 26 (see FIG. 1A). The inner diameter of the interior lumen 26 and the outer diameter of the inner catheter body 14 are mutually sized, so that the inner catheter body 14 can be fitted into and easily advanced by sliding through the interior lumen 26, up to the distal terminus of the interior lumen 26 of the outer catheter body 12.

A guide wire lumen 28 in the inner catheter body 14 (see FIG. 1C) is sized and configured to accommodate the passage of a conventional guide wire 16. A hemostatic fitting 30 on the handle 24 (see FIG. 1A) communicates with the guide wire lumen 28 to permit the introduction of the guide wire 16 into the guide wire lumen 28 axially through the inner catheter body 14. This allows the inner catheter body 14 to be introduced over a guide wire 16. The distal tip of the inner catheter body 14 may include an occluding valve or septum 32, which seals against the guide wire 16.

As FIG. 2A shows, the outer catheter body 12 also accommodates passage of the guide wire 16, so that the inner catheter body 14 can be inserted over the guide wire 16 into the outer catheter body 12. Thus, in use, both the outer catheter body 12 and the inner catheter body 14 can be introduced in tandem over a guide wire 16 into the peripheral vasculature, as FIG. 2A illustrates. The distal terminus of the interior lumen of the outer catheter body 12 may also include an occluding valve or septum 32, which also seals against the guide wire 16.

Figure 1C:
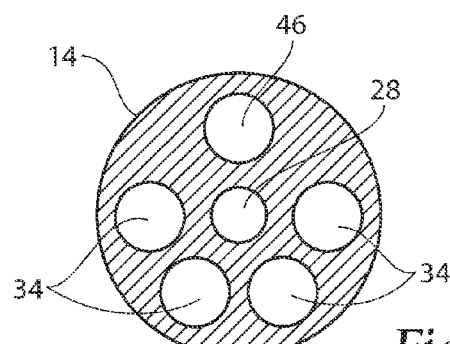
FIG. 1C is a section view of the inner catheter body taken generally along line 1C-1C in FIG. 1A.

As further shown in FIG. 1C, one or more infusion lumens 34 are formed within the inner catheter body 14. The infusion lumens 32 communicate with infusion ports 36 at the distal end of the inner catheter body 14. A standard luer lock adapter 38 on the handle 24 communicates with the infusion lumens 34. A source 40 of therapeutic agent(s) can be coupled to the adapter 38 (as exemplified in FIG. 2A). Therapeutic agent(s) in solution are conveyed through the infusion lumens 34 of the inner catheter body 14 for discharge by the ports 36 into the interior lumen 26 of the outer catheter body 12 (see FIGS. 2E and 2F).

In the illustrated embodiment, the porous fluid distribution section 18 of the outer catheter body 12 comprises an array of axially spaced-apart apertures 42 that communicate with the interior lumen 26 along the length of the porous fluid distribution section 18. The apertures 42 can comprise an array of discrete holes formed, e.g., by laser drilling, or an array of pores in a microporous membrane affixed to the distal end of the outer catheter body 12, or combinations thereof.

When the inner catheter body 14 occupies the interior lumen 26 of the outer catheter body 12 within the porous fluid distribution section 18, therapeutic agent(s) in solution discharged by the infusion ports 36 are conveyed into the interior lumen of the outer catheter body 12.

The distal end of the inner catheter body 14 carries a barrier structure 44, which can comprise e.g., an expandable body like a balloon or a coated wire mesh. In FIG. 1A, the barrier structure 44 is shown in a normally reduced dimension condition (e.g., collapsed or a low profile condition), which accommodates the sliding insertion of the inner catheter body 14 into the interior lumen 26 of the outer catheter body 12 (as FIG. 2B shows).

As FIG. 2C shows, the barrier structure 44 can be enlarged on demand toward an increased dimension condition. The barrier structure 44 can be enlarged in various ways. It can, e.g., include an umbrella-like mechanism, operated by a stylet (not shown) axially movable within the inner catheter body 14.

In the representative embodiment illustrated, the barrier structure 44 expands by introduction of an expansion medium. In this arrangement, the inner catheter body 14 includes an expansion media lumen 46, shown in FIG. 1C (in the alternative umbrella-like embodiment described, the stylet could occupy and axially slide through this lumen 46). The expansion media lumen 46 communicates with the barrier structure 44 to convey an expansion media into the barrier structure 44 to cause it to enlarge or expand. In this arrangement, a standard luer lock adapter 48 on the handle 24 communicates with the expansion media lumen 48 to accommodate coupling to a source of expansion media (e.g., a syringe 50 containing saline, as exemplified in FIG. 2A), to convey the expansion media upon demand to place the barrier structure 44 in its increased dimension condition (as FIG. 2C shows). In this arrangement, the luer lock adapter 48 on the handle 24 is also desirably able to vent the expansion media upon demand, to return the barrier structure 44 to its reduced dimension condition (as FIG. 2B shows), if repositioning or withdrawal of the inner catheter body 14 is desired.

When in its increased dimension condition (see FIG. 2C), the barrier structure 44 presses against the interior lumen 26 of the outer catheter body 12, forming a fluid tight seal. The fluid tight seal forms a barrier wall that blocks passage of the therapeutic agent(s) in a proximal flow direction (i.e., toward the handle 24) when discharged into the interior lumen. A fluid distribution chamber 52 is formed in situ within the interior lumen 26. The fluid distribution channel 52 is defined axially by the separation distance between the fluid tight seal formed by the barrier structure 44 and the distal terminus of the interior lumen 26 of the outer catheter body 12. The degree of separation can be visualized in situ by radiographic imaging of an outer radiopaque marker 54 on the outer catheter body 12 and an inner radiopaque marker 56 on the inner catheter body 14.

When discharged into the formed chamber 52 (see FIGS. 2E and 2F), the therapeutic agent(s) are distributed only by the fluid discharge apertures 42 in the porous fluid distribution section 18 that are distal to (and not proximal of) the location of the fluid tight seal formed by the barrier structure 44 when in its increased dimension condition.

By manipulation of the inner catheter body 14 relative to the outer catheter body 12, in tandem with the selective enlargement of the barrier structure 44, to thereby form the chamber 52, the effective infusion length or area of the fluid distribution section 18 of the outer catheter body 12 can be infinitely varied in situ. As FIG. 2D shows, the relative separation between the barrier structure 44 on the inner catheter body 14 and the terminus of the interior lumen 26 of the outer catheter body 12 (i.e., defining the volume of the chamber 52) can be infinitely varied (aided by radiographic visualization) by withdrawing and/or advancing the inner catheter body 14 within the outer catheter body 12 while the barrier structure 44 is in its reduced dimension condition. Once a desired separation is achieved, enlargement of the barrier structure 44 to its increased dimension condition locks the separation and forms the respective chamber 52, as FIGS. 2E and 2F illustrate.

II. Representative Use of the Assembly

FIGS. 3A to 3E illustrate use of the assembly 10 for delivering one or more therapeutic agents in solution into the peripheral vasculature. For the purpose of illustration, FIGS. 3A to 3E will be described in the context of treating an occlusion or thrombus in the vasculature, to reestablish blood flow through an affected area of the vasculature. In this way, the technical features of the assembly 10 in use can be described, e.g., to treat a peripheral arterial occlusion, or a hemodialysis graft occlusion, or a deep vein thrombosis.

Still, it should be appreciated that the assembly 10, which will be described in this particular context, is not limited in its application to the treatment of vascular occlusions. The use of the assembly 10, as will be described, is applicable to diverse situations requiring "infusion therapy," in which it is desired to deliver one or more therapeutic agents to a region of the body other than by means of an oral route. While this includes the delivery of therapeutic agents in solution into the peripheral vasculature, e.g., in systemic drug delivery, or anesthesia, it also encompasses the infusion of therapeutic agents into tissue masses or organs, e.g., during surgery and/or for oncological purposes in the treatment of tumors, and/or intramuscular infusions and/or epidural infusions.

FIG. 3A depicts for the purpose of illustration the introduction of the assembly 10 in conventional fashion over a guide wire 16 into the peripheral vasculature. When introduced, the assembly 10 comprises, as already described, the inner catheter body 14 nested within the outer catheter body 12, with the barrier structure 44 in its reduced dimension condition. In the exemplary embodiment, the assembly 10 is positioned, aided by radiographic imaging, in a region where a vascular occlusion (thrombus) treatable by a lytic agent is present.

Aided by radiographic imaging, the guide wire 16 is first passed through the vascular occlusion. Further aided by radiographic imaging, the assembly 10 is advanced over the guide wire 16 until the porous fluid distribution section 18 of the outer catheter body 12 occupies a significant portion of the vascular occlusion.

Figure 3B:
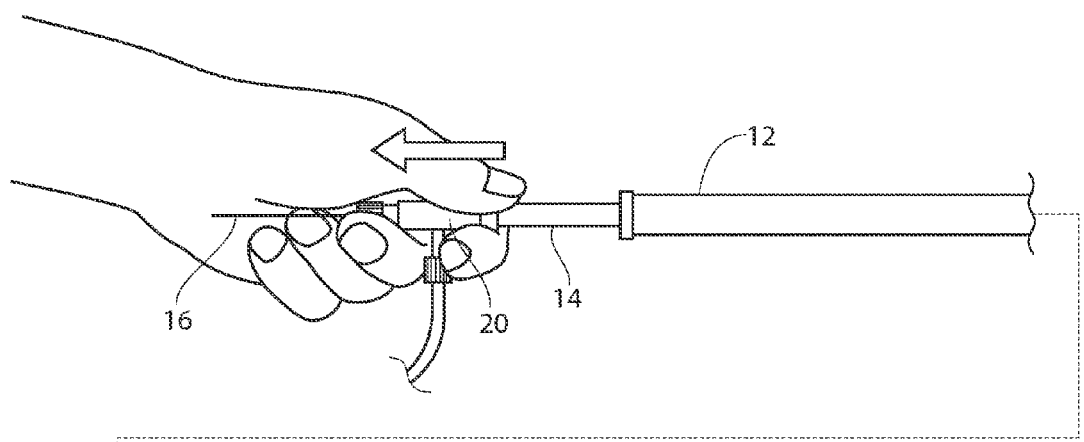
Figure 3B:
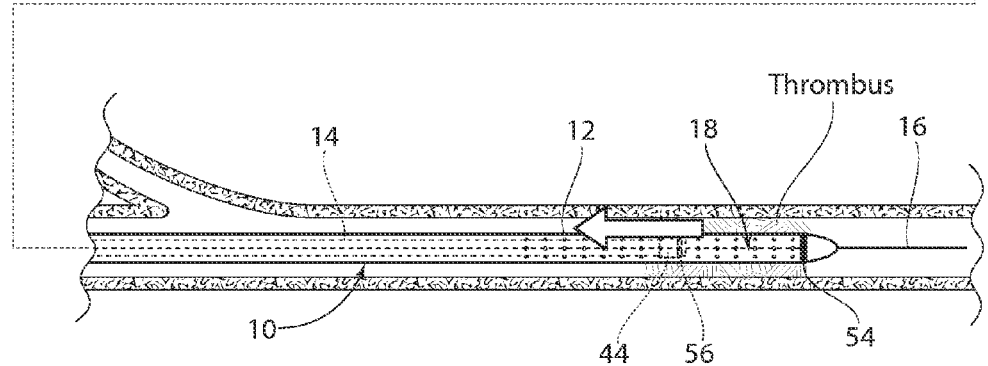
Figure 3C:
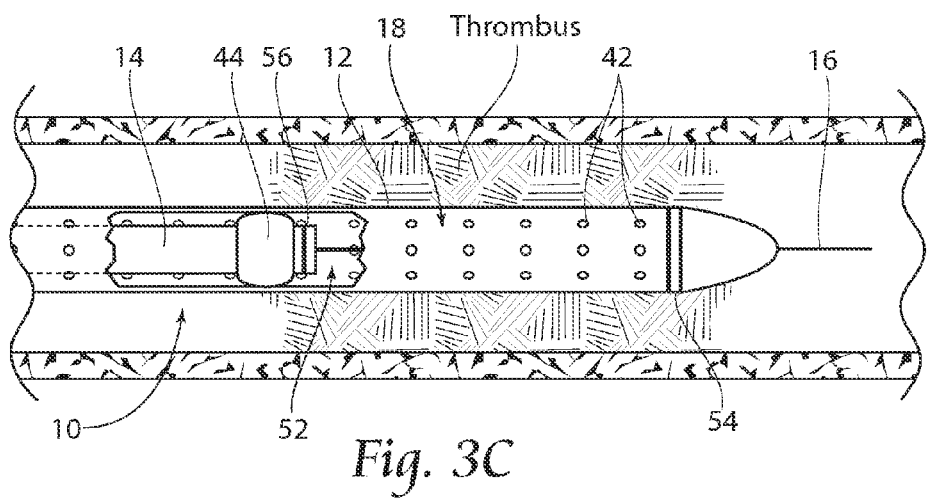

As is illustrated in FIG. 3A, the vascular occlusion possesses an axial length that is less than the maximum length of the porous fluid distribution section 18 of the outer catheter body 12. Due to the technical features of the assembly 10, the caregiver can choose to titrate the infusion length (i.e., area) of the porous fluid distribution section 18 to more closely match the length (i.e., area) of the occlusion, to thereby focus the infusion area of the assembly 10 on the therapeutic needs of the anatomic region to be treated. As FIG. 3B shows, keeping the outer catheter body 12 stationary, the caregiver manipulates the inner catheter body 14 within the outer catheter body 12 to reduce the infusion length of the porous fluid distribution section 18 of the outer catheter, by withdrawing the inner catheter body 14 within the outer catheter body 12, while gauging the separation distance of the two markers 54 and 56 by radiographic imaging.

When the separation distance visualized by the markers 54 and 56 best conforms to the morphology of the vascular occlusion (see FIG. 3C), the caregiver enlarges the barrier structure 44 to its increased dimension condition, by conveying expansion media through the inner catheter body 14 into the barrier structure 44. The barrier structure 44 enlarges toward its increased dimension condition shown in FIG. 3C. When in this condition, the barrier structure 44 presses against the interior lumen 26 of the outer catheter body 12, forming a fluid tight seal. The chamber 52 is formed.

Figure 3D:
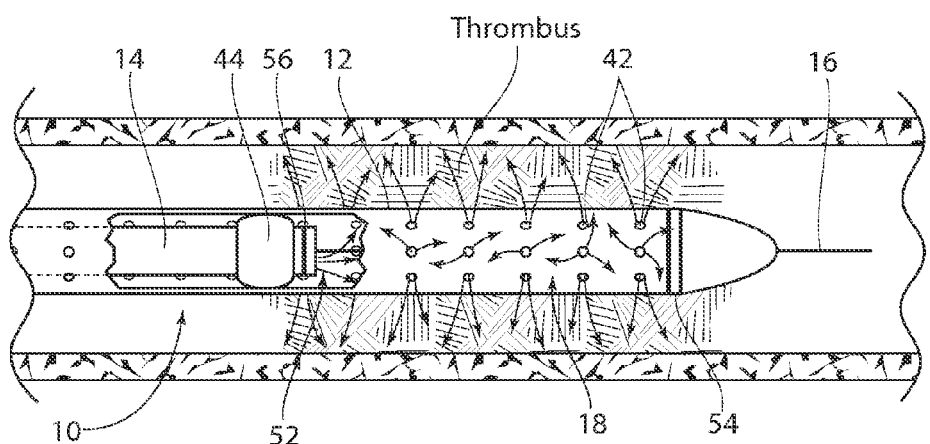
Figure 3E:
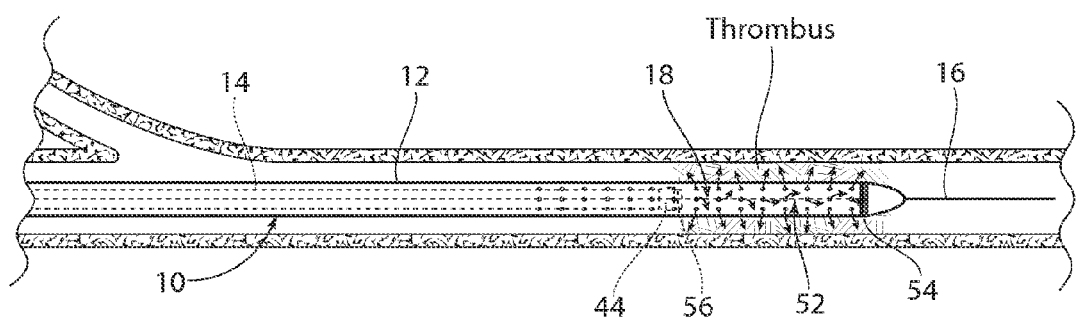

The caregiver conveys a selected lytic agent(s) through the infusion ports 36 of the inner catheter body 14 into the chamber 52 (see FIG. 3D). The chamber 52, due to its prescribed dimensions, distributes the agent(s) to only the fluid discharge apertures 42 that are distal to (and not proximal of) the location of the fluid tight seal formed by the barrier structure 44 (see FIG. 3E). This defined infusion length or area is significantly less than the maximum infusion length of the porous fluid distribution section 18, and therefore tailors the infusion area of the assembly 10 to the therapeutic needs of the anatomic region to be treated.

FIGS. 4A to 4E illustrate a different situation, in which the vascular occlusion possesses an axial length that more closely approaches the maximum length of the porous fluid distribution section 18 of the outer catheter body 12. Due to the technical features of the assembly 10, the caregiver can, using an assembly 10 that can be titrated in situ to treat a smaller occlusion shown in FIGS. 3A to 3E, choose now to instead titrate in situ the infusion length (area) of the porous fluid distribution section 18 to treat the longer occlusion shown in FIGS. 4A to 4E.

Figure 4A:
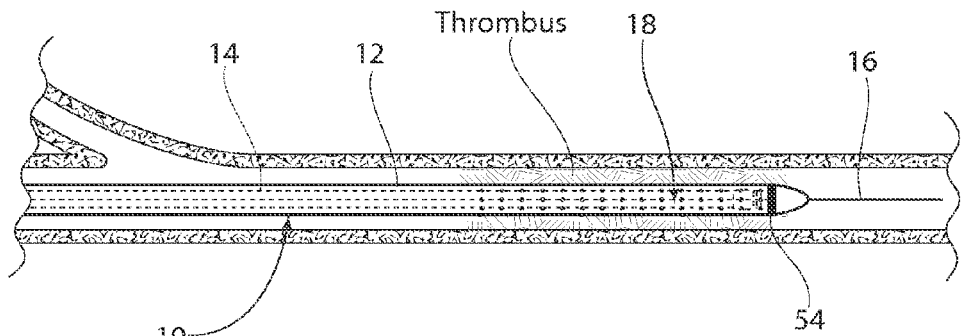
FIGS. 4A to 4E illustrate the use of the infusion catheter assembly shown in FIGS. 1A and 2A to treat an occlusion having a length longer than the length of the occlusion shown in FIGS. 3A to 3E, illustrating the capability of the infusion catheter assembly to treat only the length of the vessel desired, thereby preventing excessive drug/patient exposures.
Figure 4B:
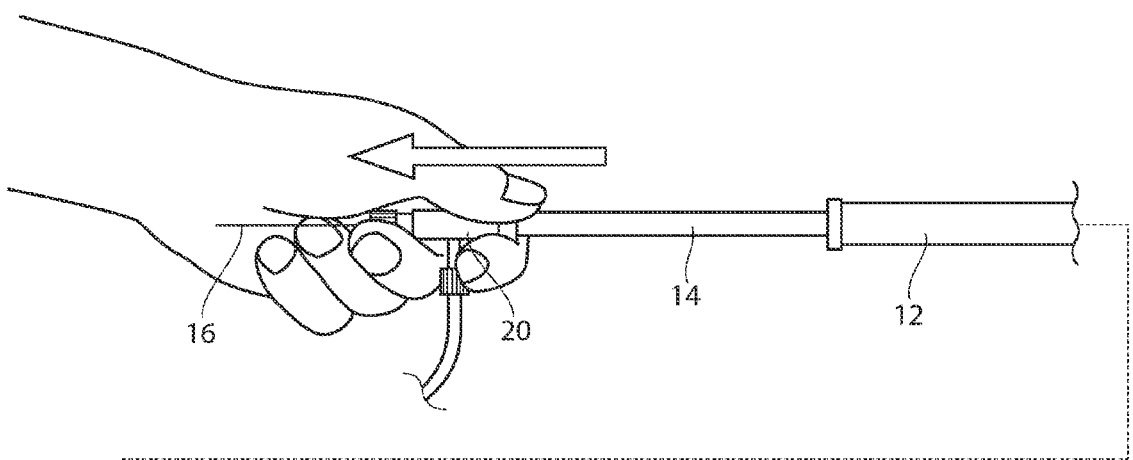
Figure 4B:
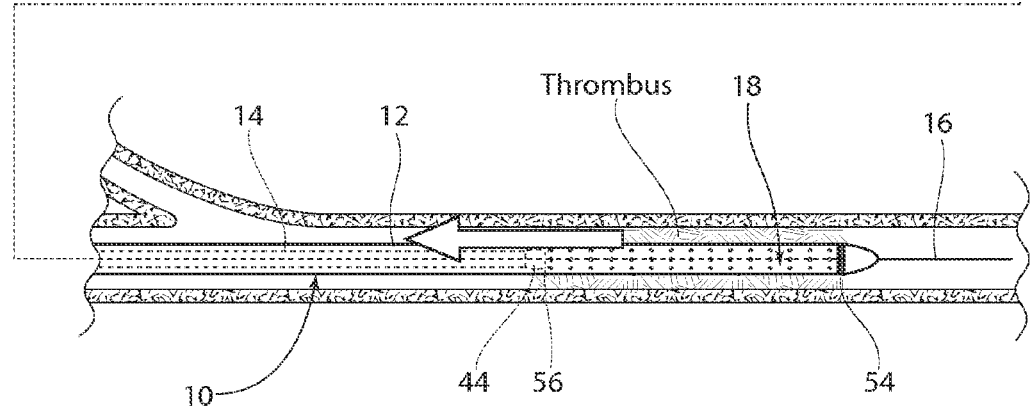

As FIG. 4B shows, with the barrier structure 44 in its reduced dimension condition, the caregiver manipulates the inner catheter body 14 within the outer catheter body 12 to increase the infusion length or area of the porous fluid distribution section 18 of the outer catheter body 12, by withdrawing the inner catheter body 14 from the outer catheter body 12 while gauging the separation distance of the two markers 54 and 56 by radiographic imaging.

Figure 4C:
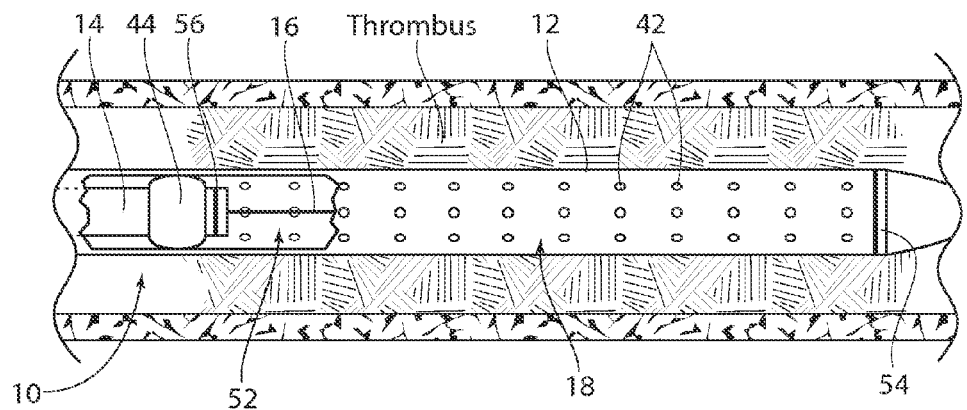
Figure 4D:
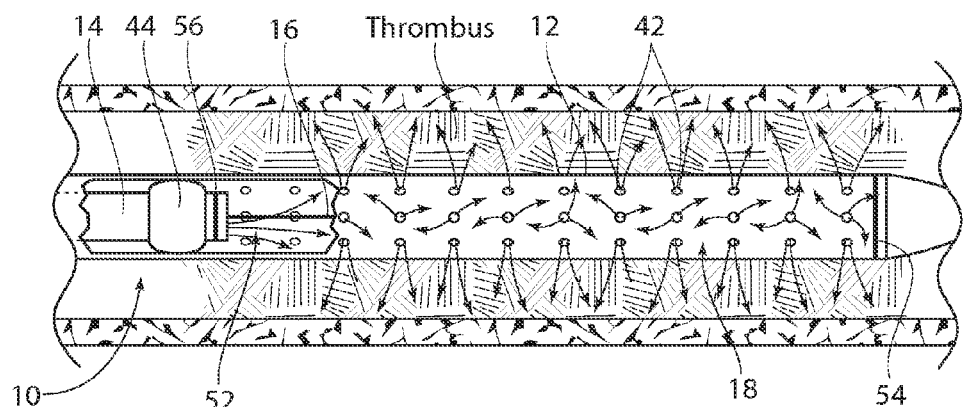

When the separation distance visualized by the markers 54 and 56 conforms to the morphology of the vascular occlusion (see FIG. 4C), the caregiver enlarges the barrier structure 44 by conveying expansion media through the inner catheter body 14 into the barrier structure 44. The barrier structure 44 enlarges toward its increased dimension condition shown in FIG. 4C. When in its increased dimension condition, the barrier structure 44 presses against the interior lumen 26 of the outer catheter body 12, forming a fluid tight seal. The chamber 52 is formed, which in FIG. 4C is significantly larger than the chamber 52 formed by manipulation of the assembly 10 in FIG. 3C.

Figure 4E:
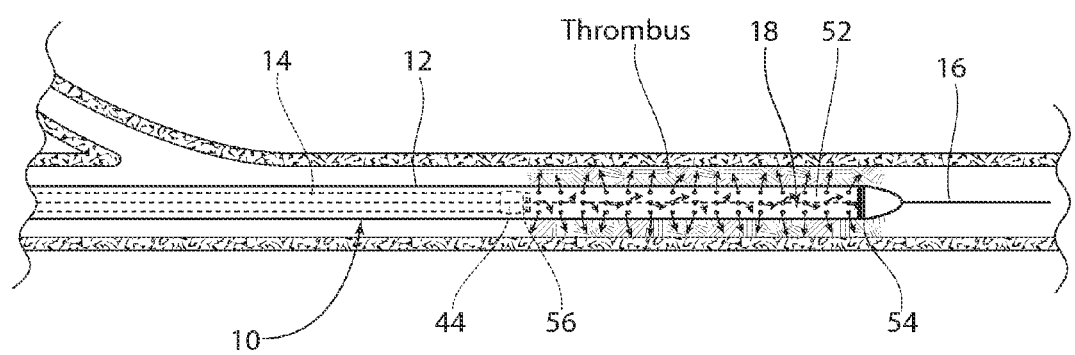

The caregiver conveys a selected lytic agent(s) through the infusion ports 36 of the inner catheter body 14 into larger chamber 52 (see FIG. 4D), which are distributed from the outer catheter body 12 by the apertures 42 of the fluid distribution section 18 that are distal to (and not proximal of) the location of the fluid tight seal of the larger chamber 52 (see FIG. 4E).

By manipulation of the inner catheter body 14 relative to the outer catheter body 12, in tandem with the selective enlargement of the barrier structure 44, the chamber volume, and thus the effective length or area of the fluid distribution section 18 of the outer catheter body 12, can be infinitely varied in situ. The relative separation between the expandable body on the inner catheter body 14 and the terminus of the interior lumen of the outer catheter body 12 (i.e., the chamber volume) can be infinitely varied by withdrawing and/or advancing the inner catheter body 14 relative to the outer catheter body 12 while the barrier structure 44 is in its reduced diameter condition. The degree of separation can be visualized in situ by radiographic monitoring of an outer radiopaque marker 54 on the outer catheter body 12 and an inner radiopaque marker 56 on the inner catheter body 14. Once a desired separation is achieved, enlargement of the barrier structure 44 to its increased dimension condition locks the separation and forms the chamber 52.

The invention thereby provides an infusion catheter assembly 10 having the ability to infinitely titrate the length of the porous distribution section 18 in situ. The infusion catheter assembly 10 provides a length of infusion that can be infinitely varied over a prescribed range, to control the effective infusion length and the rate of infusion. Using the infusion catheter assembly 10, a physician has the capability to treat only the length of the vessel desired, thereby preventing excessive drug/patient exposures.

III. Other Representative Embodiments

Figure 5:
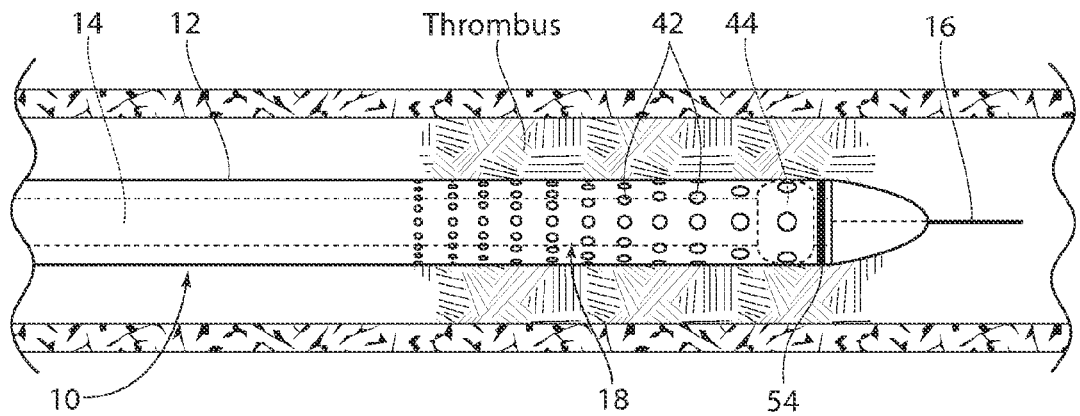
FIG. 5 is another representative embodiment of an infusion catheter assembly comprising an inner catheter body movable within an outer catheter body to infinitely titrate the length of an infusion section in situ without significantly altering a desired flow rate of infusion.

FIG. 5 shows another representative embodiment of an infusion catheter assembly 10 that provides a length of infusion that can be infinitely varied over a prescribed range, to control the effective infusion length. As before described, the assembly 10 includes an inner catheter body 14 that can be manipulated by sliding within an outer catheter body 12 along the length of a porous fluid distribution section 18. Manipulating the inner catheter body 14 relative to the outer catheter body 12 in the manner already described makes it possible to infinitely vary in situ the effective infusion length or area of the porous fluid distribution section 18 between zero up to the maximum length provided by the outer catheter body 12.

In FIG. 5, the porous fluid distribution section 18 of the outer catheter body 12 comprises an array of axially spaced-apart apertures 42, e.g., an array of discrete holes formed, e.g., by laser drilling, or an array of pores in a microporous membrane affixed to the distal end of the outer catheter, or combinations thereof. As shown in FIG. 5, the apertures 42 vary in size and/or density in a predefined fashion along the length of the porous fluid distribution section 18, so that, regardless of the effective infusion length or area of the porous fluid distribution section 18 established, the flow rate remains essentially constant. In other words, given a constant inlet fluid pressure to the inner catheter body 14, the infusion flow rate from the outer catheter body 12 remains essentially the same, independent of the effective infusion length or area.

In one exemplary embodiment (shown in FIG. 5), the apertures 42 at the distal end of the porous fluid distribution section 18 are larger in diameter (i.e., larger in size) and fewer in number (i.e., less dense) than the apertures 42 at the proximal end of the porous fluid distribution section 18. The diameter (i.e., size) and number (i.e., density) of the apertures 42 between the distal and proximal ends of the porous fluid distribution section 18 are desirably sized and configured to vary in a linear fashion along the length of the porous fluid distribution section 18 between the distal and proximal ends.

Figure 6:
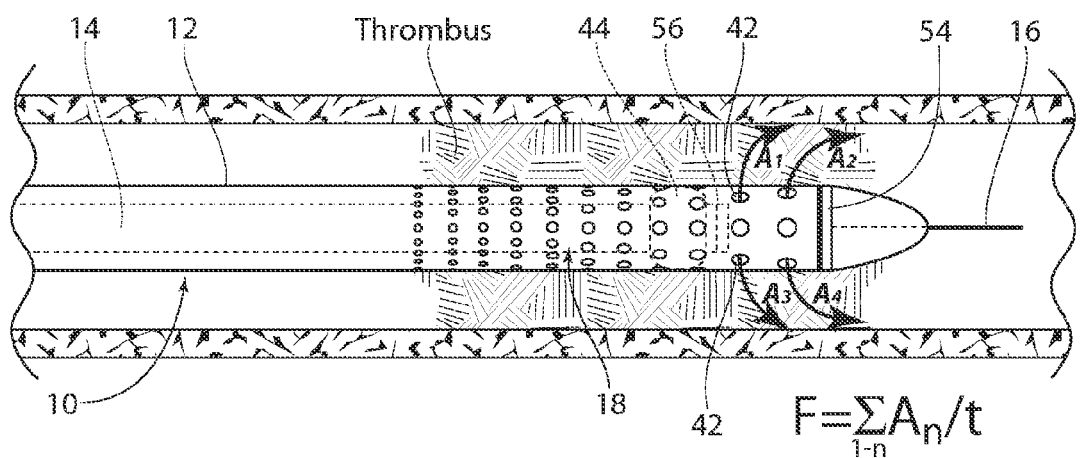
FIGS. 6 to 8 are enlarged views illustrating the manipulation of infusion catheter assembly shown in FIG. 5 to infinitely titrate the length of the infusion section in situ without significantly altering a desired flow rate of infusion (F).

As shown in FIG. 6, when the inner catheter body 14 is positioned in a sealing relationship near the distal end of the outer catheter body 12 (as previously described), fluid discharge at an established pressure from the inner catheter body 14 infuses only through the apertures 42 at the distal end of the porous fluid distribution section 18 that extend beyond the terminus of the inner catheter body 14. These distal apertures 42 are larger and less densely arranged than apertures 42 more proximally located on the porous fluid distribution section 18. The infusion flow rate (F) through the effective infusion length of the porous fluid distribution section 18 defined in FIG. 6 can be expressed as the sum of the individual fluid volumes A infused through the effective apertures 42 over a given period of time (t), or $F = \Sigma_{(1 \text{ to } n)} A_n / t$, where n equals the number of effective apertures 42.

Figure 7:
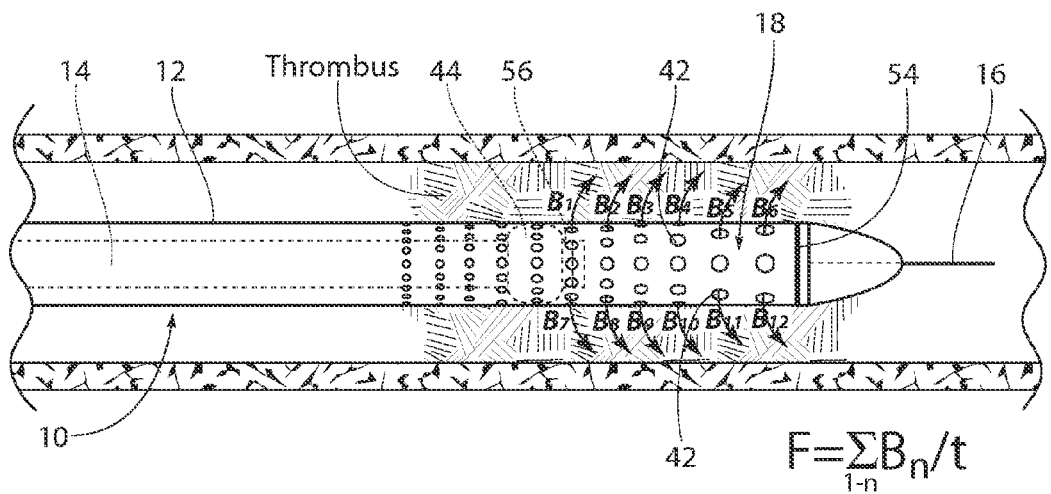

As shown in FIG. 7, when the inner catheter body 14 is positioned in a sealing relationship farther from the distal end of the outer catheter body 12, fluid discharged at the same established pressure conditions from the inner catheter body 14 will now infuse through an array of more, but purposely smaller and more densely arranged apertures 42 on the porous fluid distribution section 18. In FIG. 7, the infusion flow rate (F) through the effective infusion length of the porous fluid distribution section 18 can be expressed as the sum of the individual fluid volumes B infused through the effective apertures 42 over a given period of time (t), or $F = \Sigma_{(1 \text{ to } n)} B_n / t$, where n equals the number of effective apertures 42. In FIG. 7, the individual infusion fluid volumes B will be less than the individual fluid volumes A in FIG. 6, but the number (n) of effective apertures 42 in FIG. 7 is greater than in FIG. 6. Because the diameter (i.e., size) and number (i.e., density) of the apertures 42 between the distal and proximal ends of the porous fluid distribution section 18 are sized and configured to vary in a linear fashion with the length of the porous fluid distribution section 18, $F = \Sigma_{(1 \text{ to } n)} B_n / t$ (for the larger effective infusion length in FIG. 7) is essentially the same as $F = \Sigma_{(1 \text{ to } n)} A_n / t$ (for the smaller effective infusion length in FIG. 6).

Figure 8:
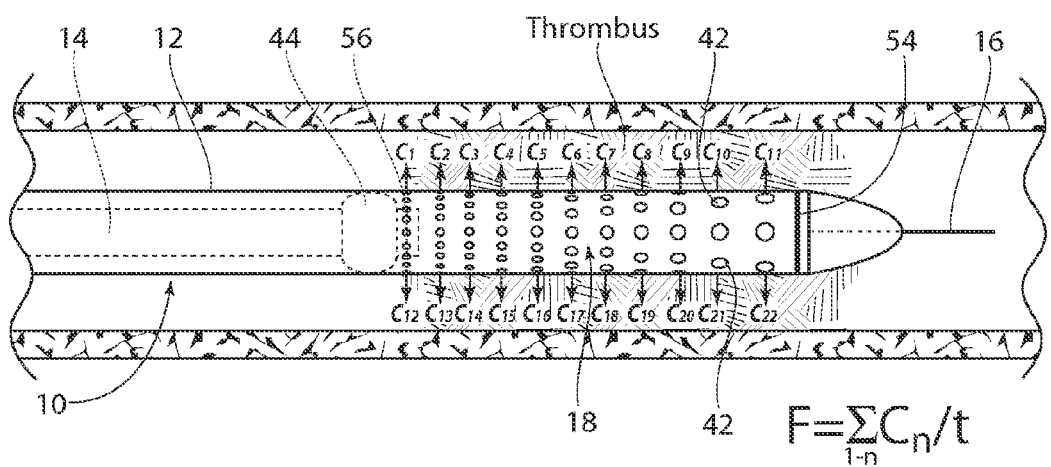

As shown in FIG. 8, when the inner catheter body 14 is positioned in a sealing relationship still farther from the distal end of the outer catheter body 12, fluid discharge at the same established pressure from the inner catheter body 14 now infuses through an array of even more, but purposely even smaller and more densely arranged apertures 42 on the porous fluid distribution section 18. In FIG. 8, the infusion flow rate (F) through the effective infusion length of the porous fluid distribution section 18 can be expressed as the sum of the individual fluid volumes C infused through the effective apertures 42 over a given period of time (t), or $F = \Sigma_{(1 \text{ to } n)} C_n / t$, where n equals the number of effective apertures 42. In FIG. 8, the individual infusion fluid volumes C will be less than the individual fluid volumes B in FIG. 7 and individual fluid volumes A in FIG. 6, but the number (n) of effective apertures 42 in FIG. 8 is greater than in FIGS. 6 and 7. Because the diameter (i.e., size) and number (i.e., density) of the apertures 42 between the distal and proximal ends of the porous fluid distribution section 18 are sized and configured to vary in a linear fashion with the length of the porous fluid distribution section 18, $F = \Sigma_{(1 \text{ to } n)} C_n / t$ (for the effective infusion length shown in FIG. 8) is essentially the same as $F = \Sigma_{(1 \text{ to } n)} B_n / t$ (for the smaller effective infusion length shown in FIG. 7), which is essentially the same as $F = \Sigma_{(1 \text{ to } n)} A_n / t$ (for the even smaller effective infusion length shown in FIG. 6).

The representative embodiment shown in FIG. 5 provides an infusion catheter assembly 10 having the ability to infinitely titrate the length of the infusion section in situ without significantly altering a desired flow rate of infusion. Using the infusion catheter assembly 10 shown in FIG. 5, a physician not only has the capability to treat only the length of the vessel desired, but also to maintain a desired flow rate of infusion to prevent excessive drug/patient exposures, independent of the effective infusion length defined.

The representative embodiment shown in FIG. 5, like the previous representative embodiments described, is applicable to diverse situations requiring "infusion therapy," in which it is desired to deliver one or more therapeutic agents to a region of the body other than by means of an oral route. While this includes the delivery of therapeutic agents in solution into the peripheral vasculature (as described), e.g., in systemic drug delivery, or anesthesia, it also encompasses the infusion of therapeutic agents into tissue masses or organs, e.g., during surgery and/or for oncological purposes in the treatment of tumors, and/or intramuscular infusions and/or epidural infusions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An infusion catheter assembly comprising:
   a catheter body having an interior lumen and including a porous fluid distribution section having a predefined maximum length communicating with the interior lumen;
   at least one fluid delivery port for dispensing a fluid from an external source into communication with the porous fluid distribution section for infusion through the porous fluid distribution section at a flow rate;
   a barrier mechanism movable within the catheter body to establish for the infusion catheter assembly an infinitely variable range of effective infusion lengths between the maximum length and any smaller length along the porous fluid distribution section; and wherein the barrier mechanism comprises an expandable structure.

2. The infusion catheter assembly according to claim 1, the expandable structure expands in response to introduction of a fluid.

3. The infusion catheter assembly according to claim 1, further including a lumen in the catheter body to accommodate passage of a guide wire, and the barrier mechanism also including a lumen to accommodate passage of the guide wire.

4. The infusion catheter assembly according to claim 1, further including a first radiopaque marker on the barrier mechanism and a second radiopaque marker on the catheter body to visualize the effective infusion length by radiographic imaging.

5. The infusion catheter assembly according to claim 1, wherein the porous fluid distribution section is sized and configured for weep or pulse-spray infusion of the fluid.

6. The infusion catheter assembly according to claim 1, wherein the catheter body is sized and configured for intravascular introduction.

7. The infusion catheter assembly according to claim 1, wherein the catheter body is sized and configured for introduction into a tissue mass or organ.

8. The infusion catheter assembly according to claim 1, wherein the catheter body is sized and configured for intramuscular introduction.

9. The infusion catheter assembly according to claim 1, wherein the fluid dispensed by fluid delivery port includes a therapeutic agent.

10. An infusion catheter assembly comprising:
    a catheter body having an interior lumen and including a porous fluid distribution section having a predefined maximum length communicating with the interior lumen, the porous discharge section comprising an array of spaced apart apertures that vary in size and/or density along the length of the porous fluid distribution section;
    at least one fluid delivery port for dispensing a fluid from an external source into communication with the porous fluid distribution section for infusion through the porous fluid distribution section at a flow rate;
    a barrier mechanism movable within the catheter body to establish for the infusion catheter assembly an infinitely variable range of effective infusion lengths between the maximum length and any smaller length along the porous fluid distribution section, and wherein the spaced apart apertures vary in size and/or density in a predetermined fashion along the maximum length such that the flow rate remains essentially constant for a given inlet pressure independent of the effective infusion length;
    wherein the barrier mechanism comprises an expandable structure.

11. The infusion catheter assembly according to claim 10, wherein the barrier mechanism comprises an expandable structure that expands in response to introduction of a fluid.

12. The infusion catheter assembly according to claim 10, further including a lumen in the catheter body to accommodate passage of a guide wire, and the barrier mechanism also including a lumen to accommodate passage of the guide wire.

13. The infusion catheter assembly according to claim 10, further including a first radiopaque marker on the barrier mechanism and a second radiopaque marker on the catheter body to visualize the effective infusion length by radiographic imaging.

14. The infusion catheter assembly according to claim 10, wherein the barrier mechanism includes an inner catheter body sized and configured to be manipulated by sliding within the catheter body along the maximum length of the porous fluid distribution section, the inner catheter body including the at least one fluid delivery port; a barrier structure carried by the inner catheter body proximal of the fluid delivery port, the barrier structure having a reduced dimension condition, which accommodates the sliding manipulation of the inner catheter body along the maximum length of porous fluid distribution section, and an increased dimension condition, which presses against the interior lumen and forms a
barrier wall that blocks flow of the dispensed fluid into communication with the porous fluid distribution section proximal of the barrier wall; and
    a mechanism to selectively reduce and increase the barrier structure within the outer catheter body anywhere along the maximum length of the porous fluid distribution section to establish for the infusion catheter assembly an infinitely variable range of effective infusion lengths between the maximum length and any smaller length along the porous fluid distribution section.

15. The infusion catheter assembly according to claim 10, wherein the porous fluid distribution section is sized and configured for weep or pulse-spray infusion of the fluid.

16. The infusion catheter assembly according to claim 10, wherein the catheter body is sized and configured for intravascular introduction.

17. The infusion catheter assembly according to claim 10, wherein the catheter body is sized and configured for introduction into a tissue mass or organ.

18. The infusion catheter assembly according to claim 10, wherein the catheter body is sized and configured for intramuscular introduction.

19. The infusion catheter assembly according to claim 10, wherein the fluid dispensed by fluid delivery port includes a therapeutic agent.

20. An infusion catheter assembly comprising:
   an outer catheter body having an interior lumen and including a porous fluid distribution section having a predefined maximum length communicating with the interior lumen;
   an inner catheter body sized and configured, when in use, to be inserted into the outer catheter body and manipulated by sliding within the outer catheter body along the maximum length of the porous fluid distribution section, the inner catheter body including at least one fluid delivery port for dispensing a fluid from an external source into communication with the porous fluid distribution section for infusion through the porous fluid distribution section;
   a barrier structure carried by the inner catheter body proximal of the fluid delivery port, the barrier structure having a reduced dimension condition, which accommodates the sliding manipulation of the inner catheter body along the maximum length of porous fluid distribution section, and an increased dimension condition, which presses against the interior lumen and forms a barrier wall that blocks flow of the dispensed fluid into communication with the porous fluid distribution section proximal of the barrier wall; and
   a mechanism to selectively reduce and increase the dimension of the barrier structure within the outer catheter body anywhere along the maximum length of the porous fluid distribution section to establish for the infusion catheter assembly an infinitely variable range of effective infusion lengths between the maximum length and any smaller length along the porous fluid distribution section; wherein the barrier structure comprises an expandable structure.

21. The infusion catheter assembly according to claim 20, further including an outer radiopaque marker on the outer catheter body and an inner radiopaque marker on the inner catheter body to visualize the effective infusion length by radiographic imagining.

22. The infusion catheter assembly according to claim 20, further including a lumen in the inner catheter body to accommodate passage of a guide wire, and the outer catheter body also including a lumen to accommodate passage of the guide wire.

23. The infusion catheter assembly according to claim 20, wherein the porous fluid distribution section comprises an array of axially spaced-apart apertures or pores that communicate with the interior lumen along the maximum length of the porous fluid discharge section.

24. The infusion catheter assembly according to claim 20, wherein the porous fluid discharge section is sized and configured for weep or pulse-spray infusion of the fluid.

25. The infusion catheter assembly according to claim 20, wherein the expandable structure expands in response to introduction of a fluid.

26. The infusion catheter assembly according to claim 20, wherein the inner and outer catheter bodies are each sized and configured for intravascular introduction.

27. The infusion catheter assembly according to claim 20, wherein the inner and outer catheter bodies are each sized and configured for introduction into a tissue mass or organ.

28. The infusion catheter assembly according to claim 20, wherein the inner and outer catheter bodies are each sized and configured for intramuscular introduction.

29. The infusion catheter assembly according to claim 20, wherein the fluid dispensed by fluid delivery port includes a therapeutic agent.

* * * * *